(12) United States Patent
Surti

(10) Patent No.: US 7,122,041 B2
(45) Date of Patent: Oct. 17, 2006

(54) CLIP DEVICE

(75) Inventor: Vihar C. Surti, Winston Salem, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 0 days.

(21) Appl. No.: 10/414,417

(22) Filed: Apr. 15, 2003

(65) Prior Publication Data
US 2004/0092978 A1    May 13, 2004

Related U.S. Application Data

(60) Provisional application No. 60/372,504, filed on Apr. 15, 2002, provisional application No. 60/424,524, filed on Nov. 7, 2002.

(51) Int. Cl.
*A61B 17/08* (2006.01)

(52) U.S. Cl. ............... 606/157; 606/151; 606/142

(58) Field of Classification Search .......... 606/200, 606/113, 127, 151, 144, 142, 157, 158
See application file for complete search history.

(56) References Cited

U.S. PATENT DOCUMENTS

| | | |
|---|---|---|
| 943,263 A | 12/1909 | Moraweck |
| 1,510,416 A | 9/1924 | Pietz et al. |
| 1,578,800 A * | 3/1926 | Brandenberger ......... 294/86.21 |
| 2,113,246 A | 4/1938 | Wappler |
| 2,384,697 A | 9/1945 | Riccardi |
| 2,968,041 A | 1/1961 | Skold |
| 3,378,010 A | 4/1968 | Codling et al. |
| 3,518,993 A | 7/1970 | Blake |
| 3,616,497 A | 11/1971 | Esposito, Jr. |
| 3,777,538 A | 12/1973 | Weatherly et al. |
| 3,882,854 A | 5/1975 | Hulka et al. |
| 3,958,576 A * | 5/1976 | Komiya ............... 606/142 |
| 4,038,987 A | 8/1977 | Komiya |
| 4,046,149 A | 9/1977 | Komiya |
| 4,169,476 A | 10/1979 | Hiltebrandt |
| 4,215,871 A | 8/1980 | Hirsch et al. |

(Continued)

FOREIGN PATENT DOCUMENTS

DE    23 30182 A1    6/1973

(Continued)

OTHER PUBLICATIONS

Copy of International Search Report for PCT Application No. PCT/US03/11496 dated Jul. 11, 2003.

(Continued)

*Primary Examiner*—Corrine McDermott
*Assistant Examiner*—Christopher D. Prone
(74) *Attorney, Agent, or Firm*—Brinks Hofer Gilson & Lione

(57) ABSTRACT

A clip device for hemostasis includes an introducing tube (outer sheath) insertable into a body cavity. An operating wire is slidably inserted into an inner sheath, which in turn is separately advanceable and retractable within the outer sheath (introducing tube). The operating wire has a distal end portion and a retainer attached to the distal end portion of the operating wire. The clip device further includes a clip having a proximal end portion and at least three arm portions extending from the proximal end portion and provided with a tendency to open. A first retainer is attached to the distal end of the clip and is matingly received by a second retainer provided on the operating wire. A clip sliding ring is provided for closing the arm portions of the clip. Methods for delivering the clip and for causing hemostasis are also provided.

18 Claims, 2 Drawing Sheets

U.S. PATENT DOCUMENTS

| | | |
|---|---|---|
| 4,367,746 A | 1/1983 | Derechinsky |
| 4,394,861 A | 7/1983 | Sciortino |
| 4,394,864 A | 7/1983 | Sandhaus |
| 4,446,865 A | 5/1984 | Jewusiak |
| 4,485,817 A | 12/1984 | Swiggett |
| 4,496,090 A | 1/1985 | Crevier et al. |
| 4,512,345 A | 4/1985 | Green |
| 4,681,107 A | 7/1987 | Kees, Jr. |
| 4,706,668 A | 11/1987 | Backer |
| 4,714,075 A | 12/1987 | Krauter et al. |
| 4,735,194 A | 4/1988 | Stiegmann |
| 4,759,364 A | 7/1988 | Boebel |
| 4,796,627 A | 1/1989 | Tucker |
| 4,821,721 A | 4/1989 | Chin et al. |
| 4,835,824 A | 6/1989 | Durham et al. |
| 4,841,888 A | 6/1989 | Mills et al. |
| 4,880,015 A | 11/1989 | Nierman |
| 4,887,612 A | 12/1989 | Esser et al. |
| 4,934,364 A | 6/1990 | Green |
| 4,945,920 A | 8/1990 | Clossick |
| 4,971,067 A | 11/1990 | Bolduc et al. |
| 4,983,176 A | 1/1991 | Cushman et al. |
| 5,015,249 A | 5/1991 | Nakao et al. |
| 5,049,153 A | 9/1991 | Nakao et al. |
| 5,062,848 A | 11/1991 | Frazee et al. |
| 5,100,418 A | 3/1992 | Yoon et al. |
| 5,112,343 A | 5/1992 | Thornton |
| 5,156,609 A | 10/1992 | Nakao et al. |
| 5,222,961 A | 6/1993 | Nakao et al. |
| 5,242,456 A | 9/1993 | Nash et al. |
| 5,300,081 A | 4/1994 | Young et al. |
| 5,304,183 A | 4/1994 | Gourlay et al. |
| 5,395,381 A | 3/1995 | Green et al. |
| 5,441,509 A | 8/1995 | Vidal et al. |
| 5,445,167 A | 8/1995 | Yoon et al. |
| 5,464,416 A | 11/1995 | Steckel |
| 5,474,567 A | 12/1995 | Stefanchik et al. |
| 5,486,185 A | 1/1996 | Freitas et al. |
| 5,514,148 A | 5/1996 | Smith, III |
| 5,527,319 A | 6/1996 | Green et al. |
| 5,540,124 A * | 7/1996 | Srhoj .................. 81/128 |
| 5,569,274 A | 10/1996 | Rapacki et al. |
| 5,601,574 A | 2/1997 | Stefanchik et al. |
| 5,634,932 A | 6/1997 | Schmidt |
| 5,695,504 A | 12/1997 | Gifford, III et al. |
| 5,700,271 A | 12/1997 | Whitfield et al. |
| 5,733,329 A | 3/1998 | Wallace et al. |
| 5,766,184 A | 6/1998 | Matsuno et al. |
| 5,766,189 A | 6/1998 | Matsuno |
| 5,782,747 A | 7/1998 | Zimmon |
| 5,895,394 A | 4/1999 | Kienzle et al. |
| 5,980,534 A * | 11/1999 | Gimpelson ............. 606/119 |
| 5,989,268 A | 11/1999 | Pugsley, Jr. et al. |
| 6,001,110 A | 12/1999 | Adams |
| RE36,720 E | 5/2000 | Green et al. |
| 6,139,555 A | 10/2000 | Hart et al. |
| 6,155,968 A | 12/2000 | Wilk |
| 6,167,605 B1 | 1/2001 | Morales |
| 6,193,733 B1 | 2/2001 | Adams |
| 6,267,776 B1 | 7/2001 | O'Connell |
| 6,350,269 B1 | 2/2002 | Shipp et al. |
| 6,352,541 B1 | 3/2002 | Kienzle et al. |
| 6,464,710 B1 | 10/2002 | Foster |
| 6,814,742 B1 * | 11/2004 | Kimura et al. ............. 606/151 |
| 2001/0049497 A1 | 12/2001 | Kalloo et al. |
| 2002/0032462 A1 | 3/2002 | Houser et al. |
| 2002/0045909 A1 | 4/2002 | Kimura et al. |
| 2002/0055750 A1 | 5/2002 | Durgin et al. |
| 2002/0062130 A1 | 5/2002 | Jugenheimer et al. |
| 2002/0128667 A1 | 9/2002 | Kobayashi et al. |
| 2002/0133178 A1 | 9/2002 | Muramatsu et al. |
| 2002/0138083 A1 | 9/2002 | Muramatsu et al. |
| 2002/0138085 A1 | 9/2002 | Muramatsu et al. |
| 2002/0151916 A1 | 10/2002 | Muramatsu et al. |
| 2002/0173805 A1 | 11/2002 | Matsuno et al. |
| 2003/0069592 A1 | 4/2003 | Adams et al. |
| 2003/0069593 A1 | 4/2003 | Tremulis et al. |
| 2005/0143767 A1 | 6/2005 | Kimura |

FOREIGN PATENT DOCUMENTS

| | | |
|---|---|---|
| DE | 298 11 510 U1 | 6/1998 |
| DE | 100 11 292 A1 | 8/2000 |
| DE | 102 11 049 A1 | 3/2002 |
| EP | 0 738 501 A1 | 10/1996 |
| WO | WO 99/20183 | 4/1999 |
| WO | WO 00/21443 | 4/2000 |

OTHER PUBLICATIONS

Copy of International Search Report for PCT Application No. PCT/US03/11820 dated Jul. 11, 2003.

* cited by examiner

CLIP DEVICE

RELATED APPLICATIONS

This claims the benefit of U.S. Provisional Application Ser. No. 60/372,504, filed Apr. 15, 2002, and U.S. Provisional Application Ser. No. 60/424,524, filed Nov. 7, 2002, both entitled "Clip Device".

TECHNICAL FIELD

The present invention relates to a clip, and more specifically to a clip that can be used to cause hemostasis of blood vessels along the gastrointestinal tract, or that can be used as an endoscopic tool for holding tissue or the like.

BACKGROUND OF THE INVENTION

Conventionally, a clip may be introduced into a body cavity through an endoscope to grasp living tissue of a body cavity for hemostasis, marking, and/or ligating. In addition, clips are now being used in a number of applications related to gastrointestinal bleeding such as peptic ulcers, Mallory-Weiss tears, Dieulafoy's lesions, angiomas, post-papillotomy bleeding, and small varices with active bleeding.

Gastrointestinal bleeding is a somewhat common and serious condition that is often fatal if left untreated. This problem has prompted the development of a number of endoscopic therapeutic approaches to achieve hemostasis such as the injection of sclerosing agents and contact thermo-coagulation techniques. Although such approaches are often effective, bleeding continues for many patients and corrective surgery therefore becomes necessary. Because surgery is an invasive technique that is associated with a high mortality rate and many other undesirable side effects, there exists a need for highly effective less invasive procedures.

Mechanical haemostatic devices have been used in various parts of the body, including gastrointestinal applications. Such devices are typically in the form of clamps, clips, staples, sutures, etc. that are able to apply sufficient constrictive forces to blood vessels so as to limit or interrupt blood flow. One of the problems associated with conventional haemostatic devices, however, is that they can only be delivered using rigid shafted instruments via incision or trocar cannula. Moreover, none of the conventional haemostatic devices are strong enough to cause permanent hemostasis.

One proposed solution is described in U.S. Pat. No. 5,766,189, which shows a clip device having a pair of arms that are provided with a tendency to open. One problem with this clip and other similar types of clips having a pair of arms is that it may often be necessary to rotate the clip to properly grasp the area to be clipped. Rotation of the clip is often hindered or complicated by the travel of the operating wire through the bends of the tube(s) used to deliver the clip. Accordingly, there is a need for a clip that can be delivered to the target area and used without having to rotate the clip to a desired orientation.

The clip of the present invention solves this and other problems by providing a clip having at least three arms.

Another problem often encountered with conventional haemostatic devices is the difficulty in securing the clip device to the delivery apparatus prior to reaching the target area within the patient, and then quickly and easily releasing the clip device from the delivery apparatus once the clip has been attached to the target site.

The clip of the present invention solves this and other problems by providing a clip having retainer system that is secured by a sliding ring.

Another problem often encountered with conventional haemostatic devices is the difficulty in properly positioning these devices to grasp the area to be clipped when the surgical site is obscured by blood or other bodily fluids. For example, when attempting to clip a bleeding vessel, the area surrounding the vessel is often filled with blood, thereby preventing the surgeon from being able to locate and/or clip the vessel. It is therefore usually necessary to flush the surgical site with saline so as to wash away any blood or other bodily fluids that may be obstructing the surgeon's visibility of the site. This procedure is ordinarily accomplished by the use of a separate catheter that has been inserted into the patient and directed to the surgical site. In addition to the need for a separate catheter, the procedure often results in delays in the clipping of the vessel because of the additional time required for inserting and positioning the catheter. Accordingly, there is a need for a clip that can be properly positioned in the target area without having to utilize a separately inserted catheter to flush the target area of blood or other bodily fluids.

The clip of the present invention solves this and other problems by providing an integrated flushing feature.

SUMMARY OF THE INVENTION

A clip device for a living tissue in a body cavity according to the present invention comprises an introducing tube that is insertable into the body cavity. Disposed within the introducing tube (also referred to as the outer sheath) is an inner sheath. The inner sheath is independently slidable within the introducing tube. In other words, the inner sheath can be advanced and retracted independently of the movement of the introducing tube. A clip is provided with a proximal end from which at least three arms extend. The arms are formed of a resilient material and are shaped such that the arms have a tendency to be in an open position.

A first retainer is attached to the proximal end of the clip. An operating wire is slidably disposed within an inner portion of the inner sheath, and has a distal end portion with a second retainer attached to the distal end thereof. The second retainer releasably mates with the first retainer to connect the clip to the operating wire.

A sliding ring is provided and is configured such that when the sliding ring is moved over the arms it holds them in a closed position. The sliding ring has a portion that is sized to contact the inner sheath so that when the inner sheath is advanced, the sliding ring slides over the arms of the clip to close them. In one embodiment, the sliding ring is removable from the clip, and in another embodiment the sliding ring cannot be removed from the clip.

In one embodiment, where the sliding ring is removable from the clip, the two retainers are joined together and the sliding ring is moved to a position such that the sliding ring covers the two retainers. As a result, the clip is joined with the operating wire. The outer sheath is advanced to a position over the clip to compress or collapse the arms within the device so that it may be passed into a channel of the scope. When the device is at the target, the outer sheath is retracted to expose the arms. The inner sheath is advanced, pushing the sliding ring over the arms so as to close the arms onto the tissue. Thereafter, when the inner sheath is retracted, the retainers are released, the device is retracted, and the clip is left behind.

In the other embodiment, the sliding ring is located between the proximal end of the clip and the arms and is not removable from the clip. The retainers are joined and the inner sheath is advanced to a position over the retainers so that the clip is joined to the operating wire. The outer sheath is advanced to a position over the clip to compress or collapse the arms within the device so that it may be passed into the channel of the scope. When the device is at the target, the outer sheath is retracted to expose the arms. The inner sheath is advanced forward, pushing the sliding ring over the arms so as to close the arms onto the tissue. Thereafter, when the inner sheath is retracted, the retainers are released, the device is retracted, and the clip is left behind.

Accordingly, an object of the present invention is to deliver a clip that can reliably grasp the tissue, but will not injure the tissue, during the treatment. In order to attain the above object, a method of delivering a clip device described above is provided. The method includes releasably attaching a clip having at least three arms to an operating wire. The operating wire is located within an inner sheath, which in turn is located within an outer sheath. The outer sheath is advanced over the arms of the clip so that the clip device can be passed into the channel of the scope. When the clip is at the target, the outer sheath is retracted to expose the arms. The inner sheath is advanced forward, pushing the sliding ring over the arms to close the arms onto the tissue. Thereafter, when the inner sheath is retracted, the retainers are released, the device is retracted, and the clip is left behind.

An additional object of the present invention is to provide a clip device having an integrated flushing feature. The flushing feature includes a port located in the forward portion of the handle. In one embodiment, the port is in fluid communication with a cavity or open volume that is disposed between the inner and outer sheaths. This cavity extends forward from the handle to the distal ends of the inner and outer sheaths. As a result, the injection of any fluid, such as saline solution, through the port in the handle is directed through the cavity and out the distal end of the outer sheath. The flushing feature permits the surgical site to be flushed of blood or other bodily fluids prior to and/or while positioning the clip to grasp the targeted tissue.

According to one method of using the flushing feature described above, the clip is first delivered to the surgical site where the targeted tissue is generally located. If it is determined that the targeted tissue is obscured by blood or other bodily fluids, then saline is injected through the port in the handle so as to pass through the cavity between the inner and outer sheaths. The saline exits the cavity at the distal end of the outer sheath, thereby flushing the area surrounding the clip of any blood or other bodily fluids. Injection of saline through the port is continued or repeated as necessary to flush the surgical site during the treatment.

DESCRIPTION OF THE INVENTION

Figure 1:
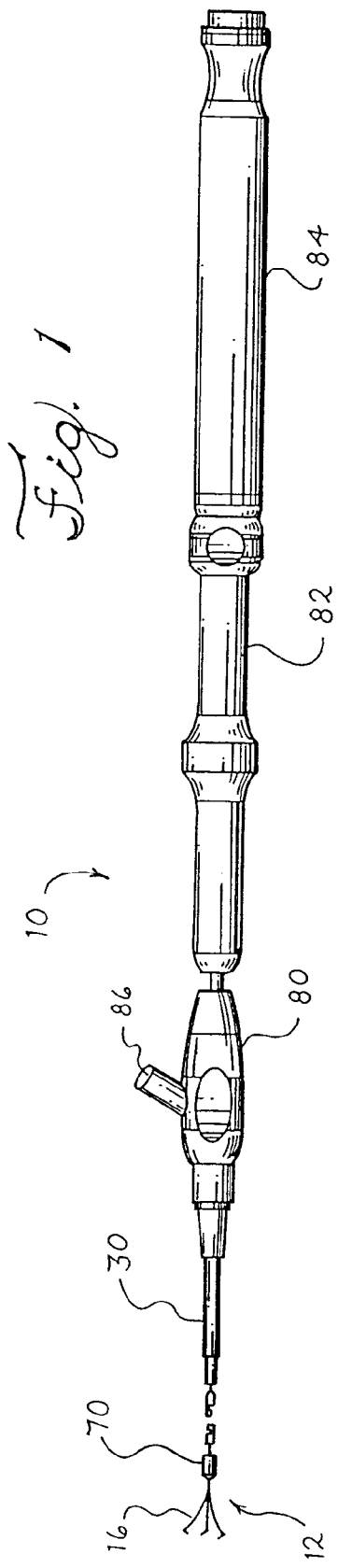
FIG. 1 is an illustration of one embodiment of the clip device according to the present invention.

The present invention provides a clip device for tissue or the like. Referring to FIG. 1, a clip device according to the present invention is shown. The clip device 10 includes a clip 12 with a proximal end 14 having at least three arms 16 extending from the proximal end. Each arm is preferably inwardly bent at its end 18 to better grasp the tissue. While three arms are preferred, it is contemplated that more than three arms may be used.

The clip may be made from any suitable resilient material such as stainless steel, nitinol, plastic, and the like. In addition, the arms may have a cross-sectional shape that is round, square, triangular, pie-shaped, truncated cone, and the like.

The proximal end 14 has a first retainer 20 attached to the arms. In one embodiment, the first retainer is permanently attached to the arms. The retainer is provided with a shape that will complement a shape provided on a second retainer so that the first and second retainers will matingly join with each other. For example, the first retainer has a first end 22 and a second end 24 with a notch 26 disposed between the first end and the second end. In one embodiment, the first retainer at the first end has a first diameter 23 and at the second end 24, the retainer is in the shape of a half-cylinder having a flat top surface 25. As will be explained in more detail below, this shape advantageously provides secure mating with a complementary second retainer without increasing the diameter beyond that of the first end of the retainer.

The clip device 10 also has an outer sheath 30 (or introducing tube) having an inner diameter that receives an inner sheath 40. The inner sheath can be advanced and retracted independently of the outer sheath. The inner sheath has an inner diameter that receives an operating wire 50 with a distal end 52.

The outer sheath is attached at its proximal end to a forward handle portion 80. The inner sheath extends through the forward handle portion 80 and is attached at its proximal end to a middle handle portion 82, which is disposed proximally of the forward handle portion. The operating wire extends through the forward and middle handle portions, and is attached at its proximal end to a rearward handle portion 84, which telescopically extends over the proximal portion of the middle handle portion. As will be explained in more detail below, longitudinal movement of the operating wire and the inner and outer sheaths with respect to each other is controlled by longitudinal manipulation of the forward, middle and rearward handles portions with respect to each other.

The forward handle portion includes a flushing port 86. The flushing port can comprise a standard male or female luer fitting, or any other valve mechanism that permits the injection of fluid therethrough. The flushing port is in fluid communication with the interior volume of the forward handle portion, which in turn is in fluid communication with a cavity or gap 88 that is disposed between the inner and outer sheaths. Accordingly, any fluid injected through the flushing port will necessarily enter the cavity between the inner and outer sheaths, and will subsequently exit the cavity near the distal end 90 of the outer sheath (see FIG. 2). In other words, the fluid injected through the flushing port will exit the clip device near the clip.

Alternatively, the cavity can be disposed inside the inner sheath, or either the inner or the outer sheath can comprise a lumen disposed therein through which fluid can be passed along the length thereof. It should also be understood that the flushing port could be alternatively located on either of the middle or rearward handle portions, or on a portion of the outer sheath distally of any of the handle portions.

A second retainer 60 is attached to the distal end of the operating wire. Preferably, the second retainer is complementary to the first retainer so that the first and second retainers can be matingly joined. Accordingly, the second retainer has a first end 62 and a second end 64 with a notch 66 disposed between the first end and the second end. In one embodiment, the second retainer at the first end has a first diameter 63 and at the second end 64, the retainer is in the shape of a half-cylinder having a flat surface 65. In addition, the first diameter of the second retainer is substantially identical to the first diameter of the first retainer.

The first and second retainers are joined with each by locating the flat surface 25 of the first retainer within the notch 66 of the second retainer and by locating the flat surface 65 of the second retainer within the notch 26 of the first retainer. Because the second end of each of the first and second retainers are each about one-half the diameter of the first diameter of their respective retainers, when joined, the first and second retainers form a substantially continuous cylinder shape having substantially the same diameter from the first end of the second retainer to the first end of the first retainer.

It will be understood by one of skill in the art that, although the first and second retainers matingly join with each other, they will not retain a joined position unless they are held together. Accordingly, in a first embodiment, a sliding ring 70 is provided. In this first embodiment, shown in FIG. 2, the sliding ring has an inner diameter slightly larger than the first diameter of the first retainer and the second retainer. In other words, the inner diameter of the sliding ring is such that the sliding ring can slide over the retainers yet hold and maintain them in a joined position. As a result, the sliding ring can slide over the first and second retainers to hold them in a mating position. In addition, the sliding ring can slide toward the ends of the arms of the clip causing the arms to move to a closed position.

Figure 3:
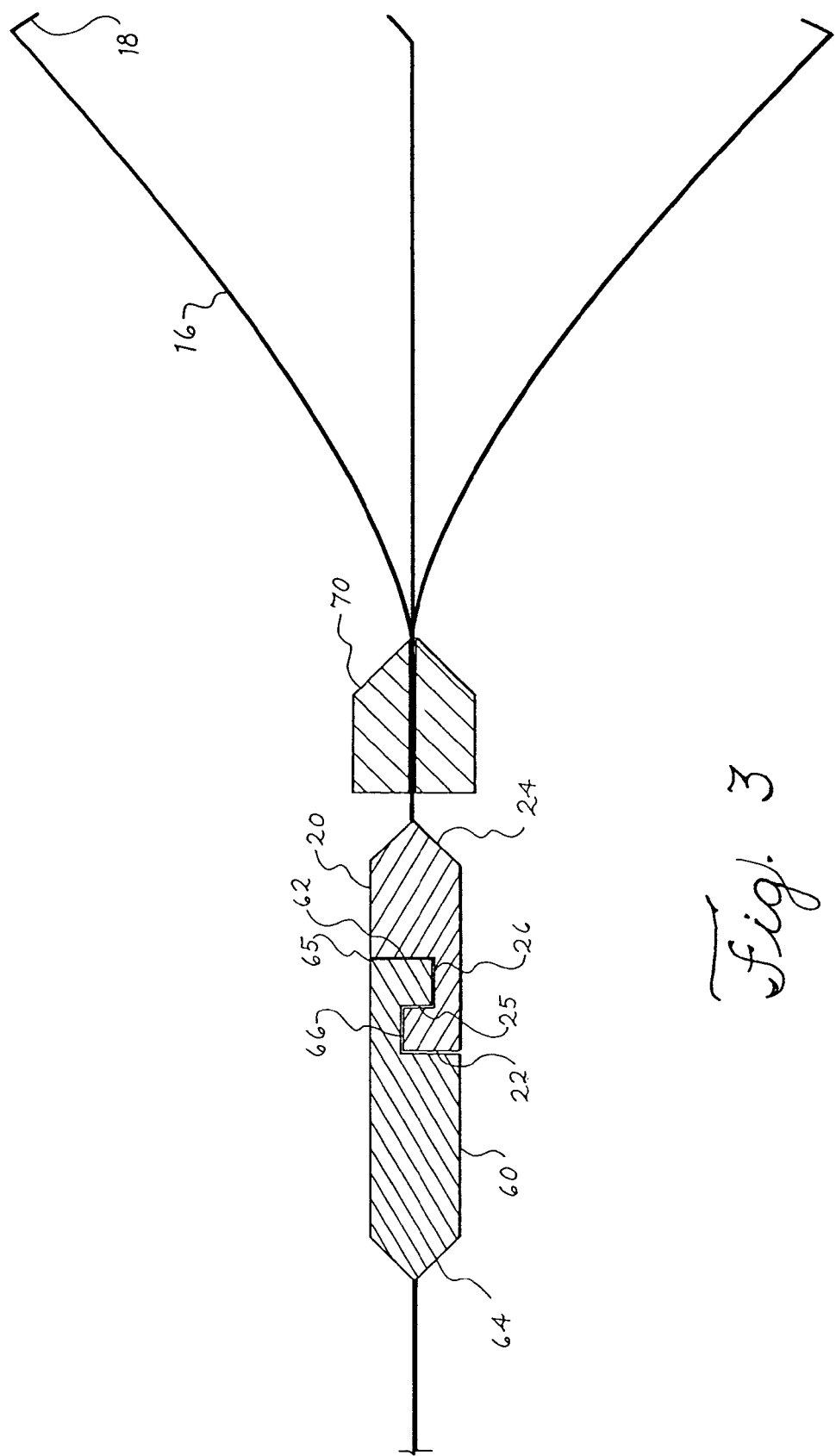
FIG. 3 is an illustration of a portion of the clip device of the present invention after the retainers are joined.

In another embodiment, shown in FIG. 3, the sliding ring has an inner diameter smaller than the first diameter on the first retainer. As a result, the sliding ring is not removable from the clip. In this embodiment, the sliding ring can be located adjacent the proximal end of the clip so that the arms are in an open position. The sliding ring can then be moved to a position toward the ends of the arms to close them.

The operation of the first embodiment will be described. The outer sheath of the clip device is retracted to expose the inner sheath, the operating wire, and the second retainer. A clip according to the present invention is provided and the first retainer is matingly joined with the second retainer. The sliding ring is pushed over the first and second retainers so that they are maintained in a joined position.

Next, the outer sheath is pushed toward the distal end of the inner sheath and beyond the clip causing the arms of the clip to close. In this state, the outer tube is introduced into a body cavity via a channel of an endoscope that has been previously inserted into the body cavity. While the body cavity is observed via the endoscope, the distal end portion of the outer sheath is guided to a part to be treated.

If the part to be treated is obscured by blood or other bodily fluids, then a fluid such as saline is injected through the flushing port on the forward handle portion. The saline enters the cavity or gap between the inner and outer sheaths, and exits the distal end of the outer sheath. The saline floods the area so as to flush any blood or bodily fluids away from the part to be treated. The injection of saline is continued and/or repeated as necessary during the following steps so as to keep the area free of blood and other bodily fluids.

Alternatively, a vacuum is applied to the flushing port so as to create suction within the cavity or gap between the inner and outer sheaths. This suction can be used to remove blood or other bodily fluids from the area surrounding the part to be treated.

Next, the outer sheath is pulled toward the proximal end (i.e., retracted) to expose the clip and the distal end portion of the inner sheath. The inner sheath is then advanced toward the clip causing the sliding ring to slide toward the arms of the clip causing the arms to close. The inner sheath is then retracted and when the distal end of the inner sheath passes the first and second retainers, they detach and release from each other and the clip is left inside the body cavity, holding the tissue. After disengaging the retainers, the clip operating device is removed from the channel of the endoscope.

The operation of the second embodiment will be described. The outer sheath of the clip device is retracted to expose the inner sheath, the operating wire, and the second retainer. A clip according to the present invention is provided and the first retainer is matingly joined with the second retainer. The sliding ring in this embodiment cannot slide is pushed toward the distal end unit so that the first and second retainers are maintained in a joined position.

Next, the outer sheath is pushed toward the distal end of the inner sheath and beyond to the clip causing the arms of the clip to close. In this state, the outer tube is introduced into a body cavity via a channel of an endoscope that has been previously inserted into the body cavity. While the body cavity is observed via the endoscope, the distal end portion of the outer sheath is guided to a part to be treated.

Next, the outer sheath is pulled toward the proximal end side to expose the clip and the distal end portion of the inner sheath. The inner sheath is then advanced toward the clip causing the sliding ring to slide toward the arms of the clip causing the arms to close. The inner sheath is then retracted and when the distal end of the inner sheath passes the first and second retainers, they detach and release from each other and the clip is left inside the body cavity, holding the tissue. After disengaging the retainers, the clip operating device is removed from the channel of the endoscope.

As noted above, the present invention also contemplates a method of delivering a clip to a target. The method includes providing a clip having a proximal end with at least three arms extending from the proximal end and with a first retainer attached to the proximal end. The first retainer is then matingly joined with a second retainer provided on a distal end of an operating wire that is disposed within an inner sheath. The inner sheath, in turn, is slidably disposed in an outer sheath. In other words, the inner sheath can be advanced or retracted independently of the outer sheath. The first retainer and the second retainer are held in a joined position by either a sliding ring or by the inner sheath.

The outer sheath is advanced so that it contacts the clip and forces the arms to a closed position. The outer sheath is then inserted into a channel of an endoscope and directed to the target site. Once at the target site, the area can be flushed by injecting saline through the flushing port. After the area has been flushed of any blood or other bodily fluids, the outer sheath is retracted to expose the clip and thereby cause the arms to extend to an open position. The clip is then directed to the specific location and then the inner sheath is advanced until it contacts the sliding ring. The inner sheath is advanced further so that the sliding ring slides over the arms causing them to close on the target. Thereafter, the inner sheath is retracted and when the inner sheath passes the second end of the second retainer, the first and second retainers release from each other. The outer sheath can then be retracted from the endoscope so that another clip can be loaded.

While there have been described what are presently believed to be the preferred embodiments of the invention, those skilled in the art will realize that changes and modifications may be made thereto without departing from the spirit of the invention. It is to be understood that the invention can be carried out by specifically different equipment and devices, and that various modifications, both as to the equipment details and operating procedures, can be accomplished without departing from the scope of the invention itself.

The invention claimed is:

1. A clip device for use in endoscopic medical procedures comprising:
   a) a first retainer configured so as to mate with a second retainer attached to a delivery system;
   b) a plurality of arms each having a proximal end and a distal end, the proximal end of each of the arms being joined to the first retainer and extending distally therefrom, each of said arms being formed of a resilient material and shaped so that the distal ends tend to be spaced apart from each other when said clip device is in an open position and adjacent to each other when said clip device is in a closed position;
   c) a sliding ring disposed about the plurality of arms, said sliding ring being movable between a first position when said clip device is in the open position and a second position when said clip device is in the closed position, said sliding ring being configured to cause the distal ends of said arms to be adjacent to each other when in the second position,
   wherein the first retainer is disposed within the sliding ring when the sliding ring is in the first position and is disposed proximally of the sliding ring when the sliding ring is in the second position, and
   wherein the first retainer is engaged with the second retainer of the delivery system, the sliding ring prevents the first retainer from disengaging from the second retainer when in the first position, and the sliding ring permits the first retainer to disengage from the second retainer when in the second position.

2. The clip device according to claim 1, wherein the sliding ring comprises a proximal portion and a distal portion, the proximal portion having a first tubular cross-section defining an interior surface that is configured to slidably engage an exterior surface of the first retainer and an exterior surface of the second retainer, and the distal portion having a second tubular cross-section that is configured to slidably engage an outer surface of each of said arms, the second tubular cross-section being smaller than the first tubular cross-section to prevent said sliding ring from being removed from a proximal end of the clip device.

3. A clip device for use in endoscopic medical procedures comprising:
   a) a first retainer configured so as to mate with a second retainer attached to a delivery system;
   b) a plurality of arms each having a proximal end and a distal end, the proximal end of each of the arms being joined to the first retainer and extending distally therefrom, each of said arms being formed of a resilient material and shaped so that the distal ends tend to be spaced apart from each other when said clip device is in an open position and adjacent to each other when said clip device is in a closed position;
   c) a sliding ring disposed about the plurality of arms, said sliding ring being movable between a first position when said clip device is in the open position and a second position when said clip device is in the closed position, said sliding ring being configured to cause the distal ends of said arms to be adjacent to each other when in the second position,
   wherein the first retainer is disposed within the sliding ring when the sliding ring is in the first position and is disposed proximally of the sliding ring when the sliding ring is in the second position, and
   wherein the first retainer comprises a proximal portion and a distal portion, the proximal portion having a hook and a notch, the hook being configured to engage a notch on the second retainer, and the notch being configured to engage a hook on the second retainer.

4. The clip device according to claim 3, wherein the distal portion of the first retainer has a circular cross-section, the hook has a semi-circular cross-section, and the notch has a semi-circular cross-section, the cross-sectional area of the hook being greater than that of the notch.

5. The clip device according to claim 4, wherein the sliding ring has a tubular cross-section defining an interior surface, the interior surface having a diameter that is approximately equal to that of the circular cross-section of the distal portion of the first retainer.

6. A clip device for use in endoscopic medical procedures comprising:
   a) a first retainer configured so as to mate with a second retainer attached to a delivery system;
   b) a plurality of arms each having a proximal end and a distal end, the proximal end of each of the arms being joined to the first retainer and extending distally therefrom, each of said arms being formed of a resilient material and shaped so that the distal ends tend to be spaced apart from each other when said clip device is in an open position and adjacent to each other when said clip device is in a closed position;
   c) a sliding ring disposed about the plurality of arms, said sliding ring being movable between a first position when said clip device is in the open position and a second position when said clip device is in the closed position, said sliding ring being configured to cause the distal ends of said arms to be adjacent to each other when in the second position,
   wherein the first retainer is disposed within the sliding ring when the sliding ring is in the first position and is disposed proximally of the sliding ring when the sliding ring is in the second position, and
   wherein said clip device comprises three equally spaced arms, each of said arms being curved along a portion between the distal end and the proximal end.

7. The clip device according to claim 6, wherein the distal end of each of said arms comprises an inwardly bent tip portion.

8. A clip device for use in endoscopic medical procedures comprising:
   a) a first retainer configured so as to mate with a second retainer attached to a delivery system;
   b) a plurality of arms each having a proximal end and a distal end, the proximal end of each of the arms being joined to the first retainer and extending distally therefrom, each of said arms being formed of a resilient material and shaped so that the distal ends tend to be spaced apart from each other when said clip device is in an open position and adjacent to each other when said clip device is in a closed position;

c) a sliding ring disposed about the plurality of arms, said sliding ring being movable between a first position when said clip device is in the open position and a second position when said clip device is in the closed position, said sliding ring being configured to cause the distal ends of said arms to be adjacent to each other when in the second position, wherein the first retainer is disposed within the sliding ring when the sliding ring is in the first position and is disposed proximally of the sliding ring when the sliding ring is in the second position, wherein the delivery system comprises an operating wire, an inner sheath, an outer sheath and a handle, the operating wire being slidably disposed within the inner sheath and attached to the second retainer, the inner sheath being slidably disposed within the outer sheath and configured to engage a proximal end of the sliding ring, and the outer sheath being configured to enclose the clip device when the clip device is in the closed position, wherein the handle includes a flushing port that is in fluid communication with an interior volume of the delivery system, and wherein the flushing port is in fluid communication with a cavity between the inner sheath and the outer sheath, the flushing port being configured to permit the ingress or egress of fluid from near the clip device.

9. The clip device according to claim 8, wherein the flushing port comprises a standard luer fitting.

10. A haemostatic clip delivery system for use in endoscopic medical procedures comprising:
   a) a delivery apparatus comprising an operating wire, an inner sheath, an outer sheath and a handle, the operating wire being slidably disposed within the inner sheath, and the inner sheath being slidably disposed within the outer sheath; and
   b) a haemostatic clip comprising a first retainer, a plurality of arms extending distally from the first retainer, and a sliding ring disposed about the plurality of arms, said arms being formed of a resilient material and shaped so that the arm tend to be spaced apart from each other, said sliding ring being configured to engage and close said arms together, wherein the handle includes a flushing port that is in fluid communication with an interior volume of the delivery apparatus, and wherein the flushing port is in fluid communication with a cavity between the inner sheath and the outer sheath, the flushing port being configured to permit the ingress or egress of fluid from near the clip device.

11. The haemostatic clip delivery system according to claim 10, wherein the flushing port comprises a standard luer fitting.

12. The haemostatic clip delivery system according to claim 11, wherein the sliding ring comprises a proximal portion and a distal portion, the proximal portion having a first tubular cross-section defining an interior surface that is configured to slidably engage an exterior surface of the first retainer and an exterior surface of the second retainer, and the distal portion having a second tubular cross-section that is configured to slidably engage an outer surface of each of said arms, the second tubular cross-section being smaller than the first tubular cross-section to prevent said sliding ring from being removed from the proximal end of the clip device.

13. The haemostatic clip delivery system according to claim 10, wherein delivery apparatus further comprises a second retainer attached to the operating wire, the second retainer being configured to engage the first retainer of the haemostatic clip so as to temporarily secure the haemostatic clip to the delivery apparatus prior to delivery of the haemostatic clip to a target site.

14. The haemostatic clip delivery system according to claim 13, wherein the sliding ring is configured to enclose the first retainer and the second retainer prior to delivery of the haemostatic clip to the target site, the sliding ring preventing the first retainer from disengaging from the second retainer, and wherein the sliding ring is movable to a second position to permit the first retainer to disengage from the second retainer when said haemostatic clip has been delivered to the target site.

15. The haemostatic clip delivery system according to claim 14, wherein the first retainer comprises a first hook and a first notch, and the second retainer comprises a second hook and a second notch, the first hook being configured to engage the second notch, and the second hook being configured to engage the first notch.

16. The haemostatic clip delivery system according to claim 15, wherein the first retainer and the second retainer each have a generally circular cross-section, the first hook and the second hook each have a semi-circular cross-section, and the first notch and the second notch each have a semi-circular cross-section, the cross-sectional area of the first hook and the second hook being greater than that of the first and the second notch.

17. The haemostatic clip delivery system according to claim 10, wherein the distal end of each of said arms comprises an inwardly bent tip portion.

18. The haemostatic clip delivery system according to claim 10, wherein said clip device comprises three equally spaced arms, each of said arms being curved along a portion between the distal end and the proximal end.

* * * * *

UNITED STATES PATENT AND TRADEMARK OFFICE
CERTIFICATE OF CORRECTION

PATENT NO. : 7,122,041 B2
APPLICATION NO. : 10/414417
DATED : October 17, 2006
INVENTOR(S) : Vihar C. Surti It is certified that error appears in the above-identified patent and that said Letters Patent is hereby corrected as shown below:

<u>In the Drawings</u>

Figure 2:
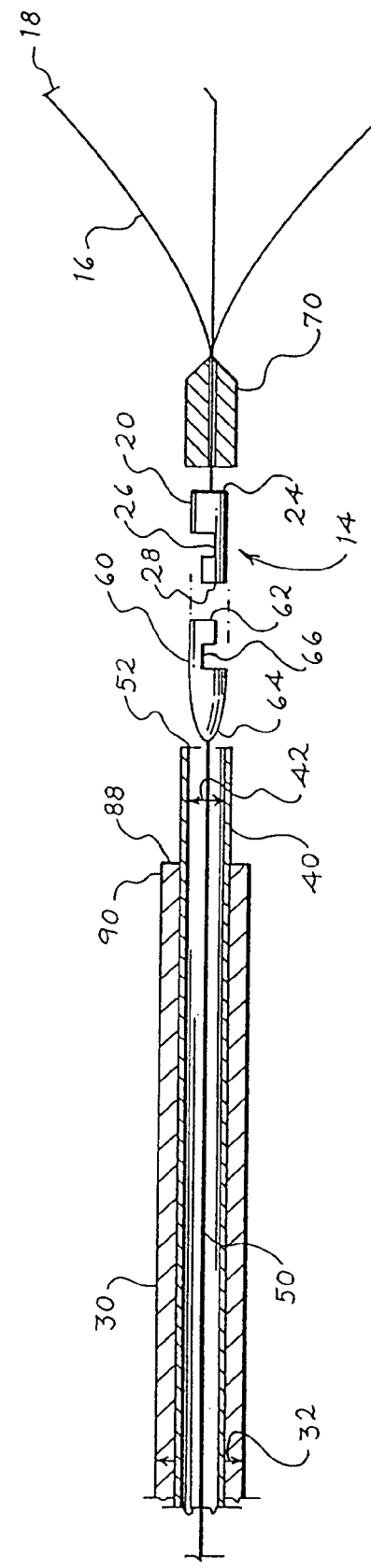
FIG. 2 is an illustration of a portion of the clip device of the present invention before the retainers are joined.

Delete original Figure 2 and replace with the corrected Figure 2 shown below.

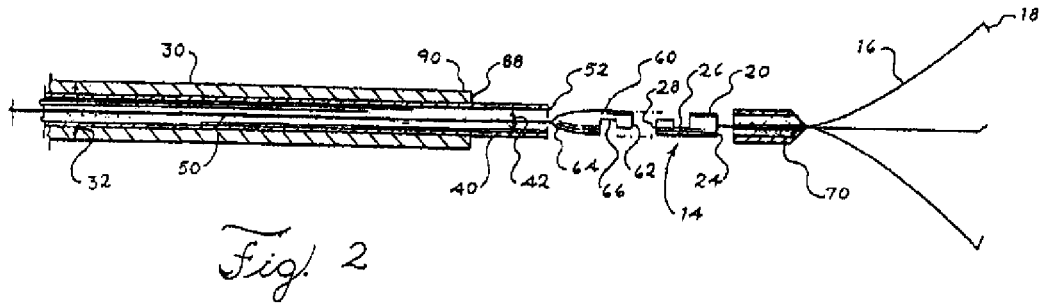

UNITED STATES PATENT AND TRADEMARK OFFICE
CERTIFICATE OF CORRECTION

PATENT NO. : 7,122,041 B2
APPLICATION NO. : 10/414417
DATED : October 17, 2006
INVENTOR(S) : Vihar C. Surti It is certified that error appears in the above-identified patent and that said Letters Patent is hereby corrected as shown below:

In the Drawings (cont'd)

Delete original Figure 3 and replace with the corrected Figure 3 shown below.

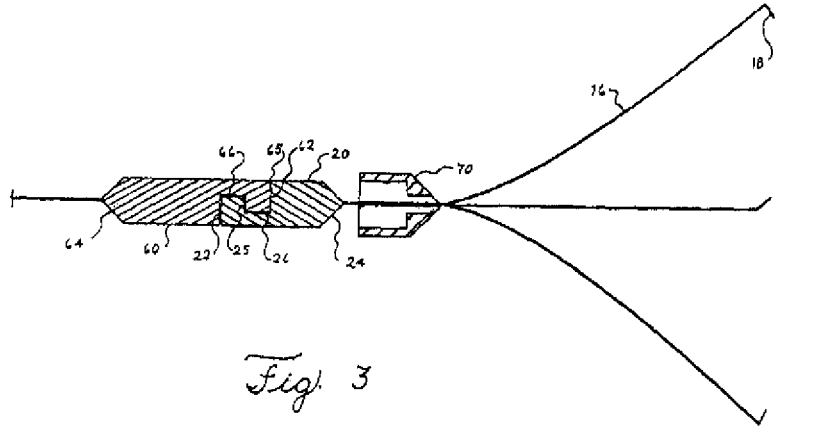

Signed and Sealed this

Twenty-fifth Day of August, 2009

David J. Kappos
*Director of the United States Patent and Trademark Office*